United States Patent [19]

Heinrich

[11] Patent Number: 4,764,523
[45] Date of Patent: Aug. 16, 1988

[54] NOVEL CARBONIC ACID ESTERS

[75] Inventor: Peter Heinrich, Binningen, Switzerland

[73] Assignee: Ciba-Geigy Corporation, Ardsley, N.Y.

[21] Appl. No.: 905,379

[22] PCT Filed: Dec. 13, 1985

[86] PCT No.: PCT/CH85/00175
§ 371 Date: Aug. 11, 1986
§ 102(e) Date: Aug. 11, 1986

[87] PCT Pub. No.: WO86/03747
PCT Pub. Date: Jul. 3, 1986

[30] Foreign Application Priority Data

Dec. 19, 1984 [CH] Switzerland ............... 6015/84
Feb. 1, 1985 [CH] Switzerland ............... 454/85

[51] Int. Cl.$^4$ .................... A61K 37/02; C07K 7/02
[52] U.S. Cl. ........................... 514/18; 530/323
[58] Field of Search ..................... 514/575, 18; 260/500.5 H; 210/638; 530/323

[56] References Cited

U.S. PATENT DOCUMENTS

| | | | |
|---|---|---|---|
| 3,634,407 | 1/1972 | Ernst et al. | 260/239.3 |
| 4,419,365 | 12/1983 | McLachlan | 514/575 |
| 4,612,122 | 9/1986 | Ambrus et al. | 210/638 |
| 4,671,901 | 6/1987 | Green | 260/500.5 H |

OTHER PUBLICATIONS

Helv. Chim. Acta 46: pp. 1385–1389 (1963).
Merck Index, 10th Ed., No. 2839, pp. 412 (1983).

*Primary Examiner*—Delbert R. Phillips
*Attorney, Agent, or Firm*—Irving M. Fishman

[57] ABSTRACT

N- and/or O-acylates, derived from carbonic acid monoesters, of desferrioxamine B of the formula $$B-NH-(CH_2)_5-N-C-CH_2CH_2-C-NH-(CH_2)_5- \quad (I)$$

with $O-AA^1$, $O-AA^2$, $O-AA^3$ substituents on the structure:

$$-N-C-CH_2CH_2-C-NH-(CH_2)_5-N-C-CH_3$$

the symbols having the following meanings:

each of $AA^1$, $AA^2$ and $AA^3$, independently of the others, is hydrogen, an acyl radical, referred to as Ac, of a carboxylic acid having from 1 to 24 carbon atoms, or an esterified oxycarbonyl radical referred to as Cb (acyl radical of a carbonic acid monoester) having a total of from 2 to 25 carbon atoms, and B has one of the meanings of Cb or, if at least one of the symbols $AA^1$, $AA^2$ and $AA^3$ represents Cb, it may also be hydrogen or an amino-protecting group referred to as X, form strong iron (III) and aluminum complexes within living cells and can therefore be used therapeutically for the treatment of warm-blooded animals, including humans, for pathological conditions associated with an excess of iron (III) or aluminum in the body or caused by iron (III)-dependent pathogenic organisms; they can also be used as intermediates for the manufacture of therapeutically effective derivatives of desferrioxamine B. The compounds according to the invention can be obtained by conventional acylation of the free amino group and/or hydroxy groups in desferrioxamine B or a suitable derivative thereof using a chloroformic ester or a similar reactive carbonic acid derivative.

17 Claims, No Drawings

NOVEL CARBONIC ACID ESTERS

The invention relates to novel derivatives, acylated by carbonic acid monoesters, of hydroxamic acids, especially of trihydroxamic acids, which are known under the name ferrioxamines and specifically desferrioxamines as metabolites of microorganisms, especially actinomycetes, and among these especially N- and/or O-acylates, derived from carbonic acid monoesters, of desferrioxamine B of the general formula

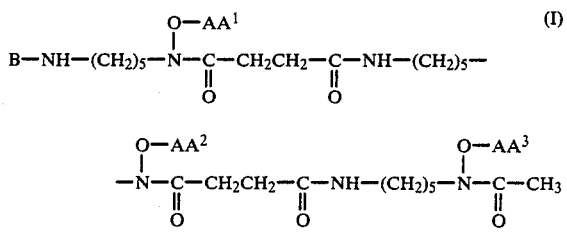

the symbols having the following meanings:

each of $AA^1$, $AA^2$ and $AA^3$, independently of the others, is hydrogen, an acyl radical, referred to as Ac, of a carboxylic acid having from 1 to 24 carbon atoms, or an esterified oxycarbonyl radical referred to as Cb (acyl radical of a carbonic acid monoester) having a total of from 2 to 25 carbon atoms, and B has one of the meanings of Cb or, if at least one of the symbols $AA^1$, $AA^2$ and $AA^3$ represents Cb, it may also be hydrogen or an amino-protecting group referred to as X, and to salts of compounds having salt-forming properties.

The invention also relates to processes for the manufacture of the above-mentioned compounds and to pharmaceutical compositions containing these compounds and processes for their manufacture; also to the use of these compounds as chemical intermediates and the therapeutic use of these compounds and pharmaceutical compositions containing them in warm-blooded animals, including humans.

Desferrioxamine B, the basic material of the acylates of the present invention, has already been known for a relatively long time (H. Bickel, H. Keberle and E. Vischer: Helv. Chim. Acta 46, 1385–9 [1963]). Its chemical structure corresponds to the formula

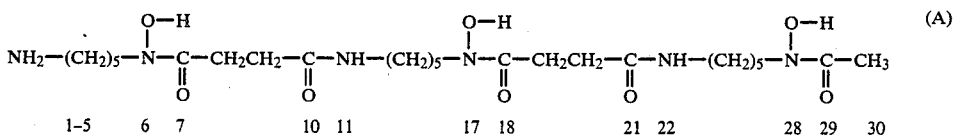

and, in accordance with Rule C-06 (replacement nomenclature) of the official IUPAC nomenclature, it has the systematic name 6,17,28-trihydroxy-7,10,18, 21,29-pentaoxo-6,11,17,22,28-pentaazatriacontylamine. (For the sake of simplicity, however, in the following the names of the acylates are derived from the trivial name, the position of individual acyl radicals in each case being related to the amino-nitrogen N or to the oxygen atoms, designated O, O' and O'', of the hydroxy groups in positions 6, 17 and 28, respectively).

Among the most striking properties of desferrioxamine B and its addition salts, which are formed with one equivalent of acid, is the ability to link up especially with trivalent metal ions, such as chromium(III), aluminium and more especially iron(III) ions to form stable chelate-like metal complexes. This imparts to desferrioxamine B the valuable pharmacological activity of preventing the deposit of iron-containing pigments in tissue and, if there are existing iron deposits in the organism, of causing the iron to be excreted, for example in the case of haemochromatosis, haemosiderosis, liver cirrhosis and poisoning with compounds of trivalent iron. The broad therapeutic use of desferrioxamine B and its salts (for example especially methanesulphonate) therefore extends generally to diseases and pathological conditions of the human body (and of the body of other warm-blooded animals) which go hand in hand with excessive loading of the organism with iron(III) ions ($Fe^{+++}$ ions), such as thalassaemia major, sickle cell anaemia, sideroachrestic anaemia, aplastic anaemia and other forms of anaemia in which haemosiderosis (that is to say a local or general increase in iron levels in otherwise undamaged body tissues) plays a part. This type also includes pathological conditions which develop in patients after several blood transfusions or repeated dialysis treatment when there is no kidney function or damaged kidney function. Owing to the complex-forming properties, desferrioxamine B has proved to have a significant activity in the case of diseases caused by iron(III)-dependent micro-organisms and parasites, such as, especially, malaria, which is of fundamental importance not only in human medicine but also in veterinary medicine. The complex formation with other trivalent metals can also be used for the excretion of those metals from the organism, for example for the removal of aluminium in the case of dialysis encephalopathy and osteomalacia, and in the case of Alzheimer's disease.

A serious disadvantage, however, is the fact that desferrioxamine and its salts have only a slight and inadequate activity when administered orally and, in the case of all the above-mentioned possible uses, they have to be administered parenterally. Thus, for example, there is recommended as a particularly effective method the administration of the active ingredient by means of a slow (8- to 12-hour) subcutaneous infusion which, however, necessitates either hospitalisation of the patient or, in the case of outpatient treatment, the use of a portable mechanical device, such as an electrically driven infusion syringe. Apart from the fact that they are complicated, such solutions involve high treatment costs which greatly restricts their use and, in particular, extensive treatment of thalassaemia in the countries of the Mediterranean, the Middle East, India and South East Asia, malaria worldwide and sickle cell anaemia in African countries is rendered impossible. These widespread diseases continue to present a serious problem for the health services in these countries and make the search for simpler and cheaper treatment, preferably by means of an orally active preparation, a priority task in this field.

Hitherto, however, no orally active forms of administration of desferrioxamine B have been described and, as regards its derivatives known hitherto, such as N,O,-O',O''-tetraacylates and N-monoacylates, there has been no relevant information on their biological activity either in the above-mentioned report by Bickel et al. or elsewhere. On theoretical grounds, it is to be assumed that, for the chelation of metal ions and thus for therapeutically applicable metal complex formation, the free hydroxy groups of desferrioxamine B make the main structural contribution. If, however, they are blocked by acylation and are therefore in practice prevented from participation in complex formation, it is to be expected that such O,O',O''-triacylates and similar compounds with blocked hydroxy groups can have complex-forming properties, and consequently the essential prerequisite for therapeutic use, only to a very slight extent if at all.

In contrast to these considerations, it has now been found that, for the same indications in which desferrioxamine B, for example in the form of commercially available Desferal ® has been effective hitherto only when administered parenterally, the above-characterised derivatives of the formula I acylated by carbonic acid monoesters (esterified oxycarbonyl radicals) surprisingly have analogous effects when administered orally, that is to say, under conditions that have hitherto been regarded as favourable but impossible.

The present invention relates especially to the acylates of the formula I defined at the beginning (including corresponding salts) which are derived from carbonic acid monoesters, especially those acylates with the following meanings of the symbols of the formula I: $AA^1$, $AA^2$ and $AA^3$ each represents a hydrogen atom, or represent acyl radicals $Ac^1$, $Ac^2$ and $Ac^3$, respectively, each of which, independently of the others, has one of the meanings of Ac, or represent oxycarbonyl radicals $Cb^1$, $Cb^2$ and $Cb^3$, respectively, each of which, independently of the others, has one of the meanings of Cb, and B is Cb or, if $AA^1$, $AA^2$ and $AA^3$ have the meanings of Cb, may also be hydrogen or an amino-protecting group referred to as X. Of these, preferred compounds of the formula I are those in which $AA^1$, $AA^2$ and $AA^3$ are identical and each represents hydrogen or the same Ac or the same Cb.

The acyl radical Ac derived from a carboxylic acid, or $Ac^1$, $Ac^2$ and $Ac^3$, corresponds to the partial formula R—CO— in which R is a hydrogen atom or a hydrocarbyl radical having from 1 to 23 carbon atoms (the acyl radical R—CO— in which R represents hydrogen is formyl).

The hydrocarbyl radical R is a saturated or unsaturated acyclic, carbocyclic or carbocyclic-acyclic hydrocarbon radical which has a maximum of 23, preferably a maximum of 17, carbon atoms. It may be unsubstituted or substituted and, instead of one, two or more carbon atoms, it may alternatively incorporate atoms of other elements (hetero atoms), such as, especially, oxygen, sulphur and nitrogen, but also, for example, phosphorus and silicon and may therefore, if these are in a cyclic radical, form a heterocyclic radical (heterocyclyl) or a heterocyclic-acyclic radical.

Radicals referred to as unsaturated are those that contain one or more multiple bonds, that is to say double and triple bonds. Cyclic radicals in which at least one 6-membered carbocyclic or 5- to 8-membered heterocyclic ring contains the maximum number of noncumulated double bonds, are referred to as aromatic. Carbocyclic radicals in which at least one ring is present as a 6-membered aromatic ring (that is to say a benzene ring) are referred to as aryl radicals.

Unless otherwise indicated, in the present disclosure acyclic radicals referred to as "lower", "medium-length" and "higher" contain from 1 to 5, 6 to 11 and 12 to 23 carbon atoms, respectively.

An acyclic hydrocarbyl radical is, for example, a straight or branched aliphatic radical which may also be mono- or poly-unsaturated, for example alkyl, alkenyl, alkadienyl, alkatrienyl or alkynyl. An alkyl radical is, for example, a lower alkyl radical (such as methyl, ethyl, propyl, isopropyl, butyl, isobutyl, sec.-butyl, tert.-butyl, pentyl or isopentyl), a medium-length alkyl radical (such as hexyl, heptyl, octyl, nonyl, decyl and undecyl) or a higher alkyl radical (for example tridecyl, pentadecyl, heptadecyl and nonadecyl). An alkenyl radical is, for example, vinyl, allyl, propenyl, isopropenyl, methallyl and 1-, 2- or 3-butenyl, also 9-decenyl and 8-heptadecenyl; an alkadienyl radical is, for example, 1,3-butadienyl, 1,3- or 2,4-pentadienyl and 8,11-heptadecadienyl; an alkatrienyl radical is, for example, 8,11,14-heptadecatrienyl; in all such radicals, individual double bonds may, independently of one another, be in the cis- or trans-configuration. An alkynyl radical is, for example, ethynyl, propargyl or 1-, 2- or 3-butynyl.

A carbocyclic hydrocarbon radical is especially a mono-, bi- or poly-cyclic cycloalkyl, cycloalkenyl or cycloalkadienyl radical, or a corresponding aryl radical containing aromatic rings. Preferred are radicals having a maximum of 12 ring carbon atoms and 3- to 8-membered, preferably 5- and/or 6-membered, rings, it also being possible for them to carry one or more acyclic radicals, for example those mentioned above, and especially the lower alkyl radicals, or further carbocyclic radicals. Carbocyclic-acyclic radicals are those in which an acyclic radical, especially one having a maximum of 7, preferably from 1 to 4, carbon atoms, carries one or more carbocyclic, optionally aromatic radicals of the above definition. Special mention should be made of cycloalkyl-lower alkyl and aryl-lower alkyl radicals, and their analogues that are unsaturated in the ring and/or side chain.

Cycloalkyl is, for example cyclopentyl and cyclohexyl, and also bicyclo[2,2,2]octyl, 2-bicyclo[2,2,1]heptyl and adamantyl, also 4,4-dimethylcyclohexyl and 2,4,4,6-tetramethylcyclohexyl; cycloalkenyl is, for example, one of the already mentioned cycloalkyl radicals, which carries a double bond in the 1-, 2- or 3-position, such as 1-, 2- or 3-cyclopentenyl and 1-, 2- or 3-cyclohexenyl. Cycloalkyl-lower alkyl or -lower alkenyl is, for example, (cyclopropyl-, cyclopentyl- or cyclohexyl-) -methyl, -1- or -2-ethyl or -vinyl, or -1-, -2- or -3-propyl or -allyl, also dicyclohexylmethyl and tricyclohexylmethyl; cycloalkenyl-lower alkyl or -lower alkenyl is, for example, 1-, 2- or 3-cyclopentenyl- or 1-, 2- or 3-cyclohexenylmethyl, -1- or -2-ethyl or -vinyl, 1-, -2- or -3propyl or -allyl.

An aryl radical is especially a phenyl radical, also a naphthyl radical, such as 1- or 2-naphthyl, a biphenylyl radical, such as, especially, 4-biphenylyl, also a tolyl radical, such as o-, m- and p-tolyl, and a xylyl radical.

Aryl-lower alkyl- and -lower alkenyl radicals are, for example, phenyl-lower alkyl or phenyl-lower alkenyl, such as, for example, benzyl, 1- or 2-phenylethyl, 1-, 2- or 3-phenylpropyl, diphenylmethyl (that is to say benzhydryl), trityl and 1- or 2-naphthylmethyl, or styryl or cinnamyl.

Heterocyclic radicals, including the heterocyclicacyclic radicals, are especially monocyclic, but also bi- or poly-cyclic, aza-, thia-, oxa-, thiaza-, thiadiaza-, oxaza-, diaza-, triaza- or tetraza-cyclic radicals of aromatic character, and also corresponding partially or completely saturated heterocyclic radicals of this type; such radicals may optionally, for example like the above-mentioned carbocyclic or aryl radicals, carry other acyclic, carbocyclic or heterocyclic radicals and may be mono-, di- or poly-substituted. The acyclic moiety in heterocyclic-acyclic radicals has, for example, the meaning given for the corresponding carbocyclic-acyclic radicals. It is especially an unsubstituted or substituted monocyclic monoaza-, monothia- or monooxa-cyclic radical, such as aziridinyl, oxiranyl and thiiranyl, and especially a heterocyclic radical of aromatic character, such as pyrryl, for example 2-pyrryl or 3-pyrryl, pyridyl, for example 2-, 3- or 4-pyridyl, also thienyl, for example 2- or 3-thienyl, or furyl, for example 2-furyl; a bicyclic monoaza-, monooxa- or monothia-cyclic radical, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl; a monocyclic diaza-, triaza-, tetraza-, oxaza-, thiaza- or thiadiaza-cyclic radical, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3- or 4-isoxazolyl, thiazolyl, for example 2-thiazolyl, isothiazolyl, for example 3- or 4-isothiazolyl or 1,2,4- or 1,3,4-thiadiazolyl, for example 1,2,4-thiadiazol-3-yl or 1,3,4-thiadiazol-2-yl; or a bicyclic diaza-, oxaza- or thiaza-cyclic radical, such as benzimidazolyl, for example 2-benzimidazolyl, benzoxazolyl, for example 2-benzoxazolyl, or benzthiazolyl, for example 2-benzthiazolyl. Corresponding partially or completely saturated radicals are, for example, tetrahydrothienyl, such as 2-tetrahydrothienyl, tetrahydrofuryl, such as 2-tetrahydrofuryl, pyrrolidinyl, such as 2-pyrrolidinyl, tetrahydropyridyl, such as 1,2,3,4- or 1,2,3,6-tetrahydropyrid-2-yl, or piperidyl, such as 2-, 3- or 4-piperidyl, also morpholinyl, thiomorpholinyl, piperazinyl and 2-N,N'-bis-lower alkylpiperazinyl, such as, especially, 2-N,N'-dimethylpiperazinyl. These radicals may also carry one or more acyclic, carbocyclic or heterocyclic radicals, especially those mentioned above. Heterocyclic-acyclic radicals are derived especially from acyclic radicals having a maximum of 7, preferably from 1 to 4, carbon atoms, for example from those mentioned above, and may carry one, two or more heterocyclic radicals, for example those mentioned above.

As has already been mentioned, a hydrocarbyl radical, (including a heterocyclyl radical) may be substituted by one, two or more substituents of the same or different type, for example free or etherified hydroxy groups, halogen atoms, (such as chlorine, fluorine or bromine), keto groups, and also free and functionally modified carboxy groups (for example carbamoyl groups and esterified carboxy groups).

An etherified hydroxy group present as a substituent in a hydrocarbyl radical is, for example, a phenoxy, benzyloxy or phenethyloxy group optionally substituted by nitro, lower alkoxy, lower alkyl or halogens, and is especially a lower alkoxy group, such as a methoxy, ethoxy, propoxy, isopropoxy, butoxy, tert.-butoxy, pentyloxy, hexyloxy and heptyloxy group.

These, especially the linear lower alkoxy groups, may in turn be substituted, especially at the terminal carbon atom, by a lower alkoxy group; such lower alkoxy-lower alkoxy groups are, for example, methoxy- or ethoxy-methoxy, 2-(methoxy- or ethoxy)-ethoxy, 2-butoxy-ethoxy, 3-(methoxy- or ethoxy)-propoxy and 4-(methoxy- or ethoxy)-butoxy. Such etherification may be repeated several times, especially in linear radicals, such as in the special case of those that are derived as recurring building blocks from simple aliphatic glycols, such as 1,4-butanediol and especially ethylene glycol, and correspond, for example, to the formula Alk(O—CH$_2$—CH$_2$—)$_n$—O— in which Alk is a lower alkyl radical and n=1 to 4, that is to say, for example, in the 2-[2-(methoxy- or ethoxy)-ethoxy]-ethoxy group or 2-{2-[2-(methoxy- or ethoxy)-ethoxy]-ethoxy}-ethoxy group. Such multi-etherified alkoxy groups are referred to simply as linear mono-, di-, tri- or poly-oxaalkoxy groups, that is to say alkoxy groups in which one, 2, 3 or more non-vicinal carbon atoms have been replaced by oxygen atoms, such as 2-oxa-propoxy, 2- and 3-oxa-butoxy, 3- and 4-oxa-pentyloxy, 3-, 4- and 5-oxa-hexyloxy, 3,6-dioxa-heptyloxy, 3,6-dioxa-octyloxy, 3,6,9-trioxa-decyloxy and 3,6,9-trioxa-undecyloxy.

An esterified carboxy group present as a substituent in a hydrocarbyl radical is especially one in which the hydrogen atom has been replaced by one of the unsubstituted carbon radicals described above, especially a lower alkyl or phenyl-lower alkyl radical (for example methoxycarbonyl, ethoxycarbonyl or benzyloxycarbonyl).

Preferred acyl radicals Ac$^1$, Ac$^2$ and Ac$^3$ are derived from unsubstituted and substituted monocarboxylic acids and dicarboxylic acids having from 1 to 20 carbon atoms. These include, on the one hand, especially radicals of acyclic monocarboxylic acids, such as alkanoyl radicals of lower alkanecarboxylic acids (for example formyl, acetyl, propionyl, butyryl, isobutyryl, valeryl, isovaleryl, pivaloyl [2,2-dimethylpropanoyl] and hexanoyl [caproyl]), of alkanoic and alkenoic acids of medium length (for example heptanoyl, octanoyl, decanoyl, undecanoyl, lauroyl or an alkenoyl radical, such as 10-undecenoyl) and of higher alkanecarboxylic acids (for example myristoyl, palmitoyl and stearoyl) or of their unsaturated analogues (alkenoyl, alkadienoyl and alkatrienoyl radicals, such as oleoyl, elaidoyl, linoleoyl [9,12-octadecadienoyl] and linolenoyl [9,12,15-octadecatrienoyl]), it being possible for all these radicals also to form substituted analogues with the above-mentioned substituents, for example halogenated, such as chlorinated and brominated, alkanoyl radicals (for example chloroacetyl, bromoacetyl and α-bromoisovaleryl), hydroxyalkanoyl radicals and their etherified analogues (for example lactoyl, ricinoleoyl [d-12-hydroxyoleoyl]or 2-methoxy- or 2-ethoxy-propanoyl), ketoalkanoyl radicals (for example levulinoyl), and also optionally esterified ω-carboxyalkanoyl radicals (especially ω-lower alkoxycarbonylalkanoyl radicals), that is to say monovalent acyl radicals of aliphatic dicarboxylic acids (for example succinic, glutaric, adipic, pimelic, suberic, azelaic, sebacic and erucic acid) which are optionally esterified at the terminal carboxy group by lower alkanols (such as methanol, ethanol or tert.-butyl alcohol) or by optionally substituted benzyl alcohols. Preferred acyl radicals also include radicals of carbocyclic and carbocyclic-acyclic carboxylic acids, especially monocyclic and bicyclic arylcarbonyl (aroyl) radicals (for example benzoyl, o, m- and p-toluoyl, and 1- or 2-naphthoyl) and araliphatic radicals, such as aralkylcarbonyl and aralkenylcarbonyl (for example phenylacetyl, 1- and 2-phenylpropionyl, and cinnamoyl), all of which may also contain in the aromatic ring from 1 to 3 identical or different substituents, such as nitro (for example 4-nitrobenzoyl), halogen, especially chlorine or fluorine (for example 4-chlorobenzoyl and 4-fluorobenzoyl), hydroxy (for example salicyloyl or 4-hydroxybenzoyl), etherified hydroxy, especially lower alkoxy, such as methoxy (for example anisoyl, veratroyl and piperonyloyl), and carboxy (for example phthaloyl, isophthaloyl and terephthaloyl), especially in esterified form, for example in the form of lower alkoxycarbonyl, such as methoxycarbonyl or ethoxycarbonyl. Preferred acyl radicals of heterocyclic carboxylic acids include, for example, 2-furoyl, 2-thenoyl, pyrrole-2-carbonyl, nicotinoyl and isonicotinoyl.

In an oxycarbonyl radical Cb, or $Cb^1$, $Cb^2$ and $Cb^3$, derived from a carbonic acid monoester, one of the two hydroxy groups of the carbonic acid is esterified by a hydrocarbyl radical that has from 1 to 24 carbon atoms and whose free valency originates from a saturated carbon atom. Such an esterified oxycarbonyl group is especially one of the partial formula $R.CH_2.O.CO$— in which R is hydrogen or may have any of the meanings indicated above for hydrocarbyl.

Preferred meanings of the O-acylating oxycarbonyl radicals $Cb^1$, $Cb^2$ and $Cb^3$ are, for example, those of the partial formula $R.CH_2.O.CO$— in which R is a cycloalkyl radical having from 5 to 7 ring members, a phenyl or phenylmethyl radical optionally mono- or poly-substituted in the ring by halogen, (especially chlorine), $C_{1-4}$-alkyl (especially methyl), $C_{1-4}$-alkoxy (especially methoxy), methylenedioxy and/or by nitro, or is especially a linear aliphatic radical, preferably one having an odd number of carbon atoms. Especially preferred as R are alkenyl and especially alkyl radicals of this type that are of medium length.

Especially preferred are also analogous radicals that are substituted at the terminal carbon atom by etherified hydroxy groups, especially those characterised and emphasised above, especially those in which one or more carbon atoms in the carbon chain of a linear alkyl radical has (have) been replaced by oxygen atoms. (If several oxygen atoms are present they are separated from one another in each case by at least one carbon atom, but preferably by more than one, especially 2, carbon atoms). There may be mentioned as examples of alkoxycarbonyl radicals Cb of this type: 2-methoxy-ethoxycarbonyl (3-oxabutoxycarbonyl), 2 ethoxy-ethoxycarbonyl (3-oxapentyloxycarbonyl), 2-(2-methoxyethoxy)-ethoxycarbonyl (3,6-dioxaheptyloxycarbonyl), 2-(2-ethoxy-ethoxy)-ethoxycarbonyl (3,6-dioxaoctyloxycarbonyl), 2-[2-(2-methoxyethoxy)-ethoxy]ethoxycarbonyl (3,6,9-trioxadecyloxycarbonyl), 4-methoxybutoxycarbonyl (5-oxahexyloxycarbonyl), 4-ethoxybutoxycarbonyl (5-oxaheptyloxycarbonyl) and 4-(2-methoxyethoxy)-butoxycarbonyl (5,8 dioxananonyloxycarbonyl).

All these preferred meanings also come into special consideration for the radical Cb as substituent of the terminal amino group; in addition, however, special mention should also be made of those that are characterised by the symbol $Cb_o$ and the partial formula $R_o.O.CO$— in which $R_o$ is a hydrocarbyl radical that can be removed under neutral conditions and/or by acidolysis; these radicals may, however, at the same time be classified as amino-protecting groups and as such are included in the meanings of the symbol X.

Such a hydrocarbyl radical $R_o$ is, for example, a mono- or bi-cyclic α-aryl-lower alkyl radical $R_a$ (that is to say one in which the aryl radical and the oxygen atom of the oxycarbonyl group are bonded to the same carbon atom of the lower alkyl radical, it also being possible for a simple heterocyclyl radical, such as 2-furyl, to be the aryl radical), especially an α-phenyl-lower alkyl or α-(2-furyl)-lower alkyl radical, especially benzyl or furfuryl respectively. Corresponding acyl radicals $R_a$—O—CO— are, for example, benzyloxycarbonyl groups that are optionally substituted in the aromatic ring by halogen atoms, nitro groups, lower alkyl groups or by lower alkoxy groups, such as unsubstituted benzyloxycarbonyl (that is to say carbobenzoxy), p-bromo- or p-chloro-benzyloxycarbonyl, p-nitrobenzyloxycarbonyl, p-methoxybenzyloxycarbonyl and p-tolyloxycarbonyl, or furfuryloxycarbonyl, and also 2-(4-biphenylyl)-2-propoxycarbonyl and similar aralkoxycarbonyl radicals described in Swiss Patent No. 509 266. These radicals can be removed, as described in more detail below, under neutral conditions by hydrogenolysis, or preferably by acidolysis.

A further hydrocarbyl radical $R_o$ of this type is a secondary or, preferably, tertiary alkyl or cycloalkyl radical $R_b$, especially one having a maximum of 12 carbon atoms, such as has also been mentioned above. A corresponding acyl radical $R_b$—O—CO— is, for example, especially a tert.-butoxycarbonyl radical, or alternatively an analogous radical, such as isopropoxycarbonyl, tert.-amyloxycarbonyl (that is to say 1,1-dimethylpropoxycarbonyl), diisopropylmethoxycarbonyl, cyclopentyloxycarbonyl, cyclohexyloxycarbonyl, d-isobornyloxycarbonyl and adamantyloxycarbonyl. These radicals can be removed, as described in more detail below, especially under acidic conditions (by acidolysis).

Yet another hydrocarbyl radical $R_o$ is a β-(trihydrocarbylsilyl)-ethoxycarbonyl radical $R_c$ which, in the β-position, carries a silyl group substituted by three unsubstituted $C_{1-6}$-hydrocarbon radicals, such as a triphenylsilyl, a dimethyl-butylsilyl or especially a trimethylsilyl group. Corresponding acyl radicals $R_c$—O—CO—, that is to say β-(trihydrocarbylsilyl)-ethoxycarbonyl radicals, such as a β-(tri-lower alkylsilyl)-ethoxycarbonyl radical, for example especially β-(trimethylsilyl)-ethoxycarbonyl, form with the amino group to be protected corresponding β-trihydrocarbylsilylethoxycarbonylamino groups (for example the β-trimethylsilylethoxycarbonylamino group). Although they are stable under the conditions of acid hydrolysis and hydrogenolysis they can be removed under quite specific very mild conditions by the action of fluoride ions, as described in more detail below.

Special mention should also be made of allyl as a hydrocarbyl radical $R_o$. The corresponding allyloxycarbonyl radical can be removed not only by acidolysis but, especially, also under very mild neutral conditions using dimedone or by the specific reducing action of tributyltin hydride with catalysis using a palladium-(O)-tetrakis-(triphenylphosphine) complex.

The complete meaning of the symbol X includes, however, other amino-protecting groups of different types and corresponds in scope to that of the amino-protecting groups that are used in the synthesis of the peptide chain and, together with corresponding methods for their removal, are described in detail in synoptical reviews and reference works such as HoubenWeyl: Methoden der organischen Chemie; 4th edition, volume 15/I and II, E. Wunsch (editor): Synthese von Peptiden (Georg-Thieme Verlag, Stuttgart; 1974). It is preferable to use amino-protecting groups that can be removed by acidolysis and under neutral conditions.

There also comes into consideration as a suitable amino-protecting group X a trityl (triphenylmethyl) group that is substituted by methyl, methoxy, halogens and/or by nitro but that is preferably unsubstituted and that can be removed by solvolysis (acidolysis) under very mild conditions, such as with only approximately 50 % acetic acid.

There should also be mentioned as amino-protecting groups X phenylsulphenyl groups that are substituted in the ring, especially the 2-nitrophenylsulphenyl group o—$O_2N$—$C_6H_4$—S—; not only can the last-mentioned group, for example, be removed by acid-catalysed solvolysis or acidolysis, in which case it is sufficient to use pyridinium chloride as acid, but it will also respond to mild mercaptolysis, for example using phenyl mercaptan, under neutral conditions.

There should also be mentioned as an aminoprotecting group X formyl, which can be removed not only under acidic conditions but also by oxidation with hydrogen peroxide.

The more specific choice of protecting group X depends on the particular properties of the acyl groups $Ac^1$, $Ac^2$, $Ac^3$, or $Cb^1$, $Cb^2$ and $Cb^3$, and especially on their stability under the reaction conditions for the removal of the protecting group.

Salts of compounds of the above formula I having salt-forming properties are derived especially from those compounds in which B represents hydrogen and are acid addition salts, especially pharmaceutically acceptable non-toxic acid addition salts with inorganic acids, for example hydrochloric acid, hydrobromic acid, sulphuric acid or phosphoric acids, or with organic acids, such as sulphonic acids, such as aromatic sulphonic acids, for example benzenesulphonic acid, p-toluenesulphonic acid or naphthalene-2-sulphonic acid, or especially aliphatic sulphonic acids, for example methanesulphonic acid, ethanesulphonic acid, 2-hydroxyethanesulphonic acid and ethane-1,2-disulphonic acid, and also carboxylic acids, for example acetic acid, propionic acid, glycolic acid, succinic acid, maleic acid, hydroxymaleic acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid.

Owing to the close relationship between the novel compounds in free form and in the form of their salts, including also those acid addition salts that may be used as intermediates, for example in the purification of the novel compounds or for their identification, hereinbefore and hereinafter the free compounds are also optionally to be understood as the corresponding salts where appropriate with regard to meaning and purpose.

The compounds of the present invention have valuable properties, especially pharmacological actions, since they exhibit a physiological action which, in its basic character, is similar to the action of desferrioxamine B. They can therefore be used in the same kind of therapeutic indications as the latter, but with the considerable advantage of oral administration, for example especially for the treatment of functional disorders in which the concentration of trivalent iron ($Fe^{3+}$ ion) in body cells is abnormally high, such as in the case of haemochromatosis and haemosiderosis. Since, in addition and also in a similar manner, they also bind aluminium ions, such as, for example, in the case of dialysis encephalopathy, osteomalacia and Alzheimer's disease, they can also be used successfully in these fields of indication.

Especially preferred compounds of the formula I for this use are especially those in which $AA^1$, $AA^2$ and $AA^3$ all have the same meaning as Cb, especially one of the meanings emphasised above for $Cb^1$, $Cb^2$ and $Cb^3$, it being possible for B also to have one of these meanings of Cb, preferably an identical meaning, but it represents especially hydrogen. There may be mentioned as such especially preferred oxycarbonyl radicals Cb, or $Cb^1$, $Cb^2$ and $Cb^3$, for example alkoxycarbonyl radicals whose carbon chain may be interrupted by 1, 2 or more oxygen atoms, that is to say, lower alkoxycarbonyl radicals (such as methoxy-, ethoxy-, propoxy-, isopropoxy-, butoxy-, i-butoxy-, sec.-butoxy-, tert.-butoxy-, pentyloxy-, isopentyloxy and hexyloxy-carbonyl), medium-length alkoxycarbonyl and alkyleneoxycarbonyl radicals (such as heptyloxy-, octyloxy-, nonyloxy-, decyloxy- and undecyloxy-, or 10-undecenyloxy-carbonyl) and also higher alkoxycarbonyl radicals and analogous mono-, di- or polyunsaturated radicals (such as, especially, dodecyloxy-, tetradecyloxy-, hexadecyloxy- and octadecyloxy-, or cis- or trans-9-octadecenyloxy-, -9,12-octadecadienyloxy- and -9,12,15-octadecatrienyloxy-carbonyl), also benzyloxy-, 2-phenylethoxy- and cinnamyloxycarbonyl, which may all be substituted in the ring in the manner emphasised above. There may be mentioned as examples of such compounds: N,O,O',O''-tetra-(ethoxycarbonyl)-desferrioxamine B and O,-O',O''-tri-(ethoxycarbonyl)-desferrioxamine B, N,O,-O',O''-tetra-(propoxycarbonyl)-desferrioxamine B and O,O'O''-tri-(propoxycarbonyl)-desferrioxamine B, N,O,O',O''-tetra-(butoxycarbonyl)-desferrioxamine B and O,O',O''-tri-(butoxycarbonyl)-desferrioxamine B, N,O,O',O''-tetra-(3-oxabutoxycarbonyl)-desferrioxamine B and O,O',O''-tri-(3-oxa-butoxycarbonyl)-desferrioxamine B, N,O,O',O''-tetra(hexyloxycarbonyl)-desferrioxamine B and O,O',O''-tri-(hexyloxycarbonyl)-desferrioxamine B, N,O,O',O''-tetra-(3,6-dioxaheptyloxycarbonyl)-desferrioxamine B and O,O',O''-tri-(3,6-dioxaheptyloxycarbonyl)-desferrioxamine B, N,O,O',-O''-tetra-(octyloxycarbonyl)-desferrioxamine B and O,O',O''-tri-(octyloxycarbonyl)-desferrioxamine B, N,O,O',O''-tetra-(3,6,9-trioxadecyloxycarbonyl)-desferrioxamine B and O,O',O''-tri-(3,6,9-trioxadecyloxycarbonyl)-desferrioxamine B, N,O,O',O''-tetra-(10-undecenyloxycarbonyl)-desferrioxamine B and O,O',-O''-tri-(10-undecenyloxycarbonyl)-desferrioxamine B, N,O,O',O''-tetra-(dodecyloxycarbonyl)-desferrioxamine B and O,O',O''-tri-(dodecyloxycarbonyl)-desferrioxamine B, and also N,O,O',O''-tetra-(octadecyloxycarbonyl) desferrioxamine B and O,O',O''-tri-(octadecyloxycarbonyl)desferrioxamine B, also N-tert.-butoxycarbonyl-O,O',O''-tri-(butoxycarbonyl)-desferrioxamine B, N-tert.-butoxycarbonyl-O,O',O''-tri-(3-oxabutoxycarbonyl)-desferrioxamine B, N-tert.-butoxycarbonyl-O,O',O''-tri-(hexyloxycarbonyl)-desferrioxamine B, N-tert.-butoxycarbonyl-O,O',O''-tri-(3,5-dioxaheptyloxycarbonyl)-desferrioxamine B and N-tert.-butoxycarbonyl-O,O',O''-tri-(octyloxycarbonyl)-disferrioxamine B.

There also come into consideration for therapeutic use mixed acylates of the formula I, especially those in which B represents hydrogen or Cb, and $AA^1$, $AA^2$ and AA³ have the meanings of Cb but not the same meaning for all symbols. Of these mixed O,O',O''-triacylates (and also N,O,O',O''-tetraacylates) there are preferred especially those in which the oxycarbonyl radicals Cb¹, Cb² and Cb³ are based on one of the unsubstituted linear aliphatic hydrocarbyl radicals given special emphasis above, at least one of them being a medium-length or higher aliphatic hydrocarbyl radical. (These especially preferred hydrocarbyl radicals are analogous to the acyl radicals of naturally occurring fatty acids, but instead of the carbonyl radical they have methylene). Normally, however, such mixed acylates are constituents of practically inseparable mixtures with other isomers in which, although the same three acyl radicals Cb¹, Cb² and Cb³ are present, each one can esterify any one of the three hydroxy groups. Accordingly, the description an O,O',O''-(Cb¹, Cb², Cb³)desferrioxamine B'', such as, for example, O,O',O''(tetradecyloxycarbonyl, hexadecyloxycarbonyl, octadecyloxycarbonyl)-, O,O',O''-(dibutoxycarbonyl, octyloxycarbonyl)-, O,O',-O''-(diethoxycarbonyl, cis-9-octadecenyloxycarbonyl)- and O,O',O''-(pentyloxycarbonyl, di-10-undecenyloxycarbonyl)-desferrioxamine B, is not only to be understood as a name for an individual compound with a non-specific assignment of the acyl groups with respect to individual oxygen atoms, but is also to be interpreted as a collective term for the whole isomeric mixture containing all the isomeric compounds with any combination of O, O' and O'' with Cb¹, Cb² and Cb³. Analogously combined polyacylates and their isomeric mixtures occur very frequently in nature, for example in the form of waxes and fats, in particular triglycerides, and it is known that, because of the basic similarity between the fatty acids, it is in practice irrelevant as regards the overall properties of an acylate whether a specific hydroxy group is esterified by one or by another acyl radical from the choice given. Individual isomers are so similar in their physical, chemical and biological behaviour that the properties of such an isomeric mixture generally correspond to the average value of the separate contributions of the individual components (acyl radicals). The individual components of such a mixture and, after hydrolysis, the individual acyl radicals, can be analytically determined, both qualitatively and quantitatively by modern analytical methods of separation, such as gas chromatography (GLC) or high-pressure liquid chromatography (HPLC), but for general characterisation conventional analytical methods, such as are common, for example, in the technology of fat processing, such as the determination of the acid number, hydrolysis number, hydrogenation number or iodine number etc., are often sufficient.

The compounds of the present invention can also be used as valuable intermediates for the manufacture of other therapeutically valuable compounds.

Especially preferred for this use are, for example, those of the compounds of the formula I in which B represents a readily removable oxycarbonyl radical $Cb_o$ which can be used as an amino-protecting group and AA¹, AA² and AA³, which may be different from one another but are preferably all the same, represent hydrogen atoms or, especially, acyl radicals Ac¹, Ac² and Ac³ and also esterified oxycarbonyl radicals Cb¹, Cb² and Cb³ having the above-mentioned general and especially emphasised meanings. More especially preferred are those compounds in which $Cb_o$ has one of the meanings given special mention above and is especially tert.-butoxycarbonyl (BOC), 2-(trimethylsilyl)-ethoxycarbonyl or allyloxycarbonyl. In so far as they carry acyl radicals Ac¹, Ac² and Ac³, these compounds are important starting materials for O,O',O''-triacylates of desferrioxamine B having a free terminal amino group, into which they can be converted by conventional removal of the amino-protecting group $Cb_o$. There come into consideration for this purpose especially those compounds in which Ac¹, Ac² and Ac³ each represents the same acyl radical, especially one of those mentioned above, which is derived from an unsubstituted, preferably saturated, aliphatic monocarboxylic acid having a maximum of 18 carbon atoms, especially those in which Ac¹, Ac² and Ac³ each represents acetyl, butyryl, pivaloyl, hexanoyl, octanoyl, palmitoyl or stearoyl, and also those in which Ac¹, Ac² and Ac³ each represents a monocyclic aroyl or aryl-lower alkanoyl radical, especially benzoyl or phenylacetyl, it being possible for these to be substituted in the ring by methyl, methoxy, chlorine and/or by nitro, although they are preferably unsubstituted. If, in such compounds of the formula I that can be used as intermediates, B represents $Cb_o$ and AA¹, AA² and AA³ all represent hydrogen, these compounds are especially suitable for the selective functionalisation of the three free hydroxy groups, whether it be for the subsequent introduction of the above-mentioned acyl groups Ac¹, Ac² and Ac³ or of the oxycarbonyl groups Cb¹, Cb² and Cb³ according to the subsequent treatment according to the present invention or for another functional conversion.

The compounds mentioned in the Examples are especially preferred.

According to the invention, compounds of the formula I are manufactured using conventional analogy processes, for example those generally known from peptide chemistry, as follows: a compound of the formula

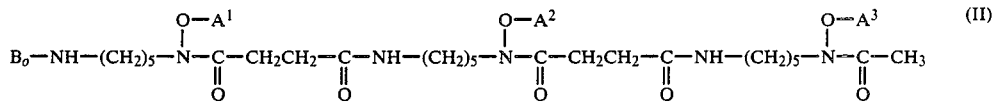

in which each of A¹, A² and A³, independently of the others, is hydrogen or has one of the above-defined meanings of Ac, and $B_o$ is hydrogen or, if at least one of the symbols A¹, A² and A³ is hydrogen, it may also be an amino-protecting group $X_o$ other than the above-defined radical $Cb_o$, is acylated using a reactive derivative of a carbonic acid monoester derived from the above-defined radical Cb, and, if desired, a resulting end product of the formula I in which at least one of the symbols AA¹, AA² and AA³ represents Ac or Cb and B has one of the meanings of Cb is converted by ammonolysis into a compound of the formula I in which B represents Cb and AA¹, AA² and AA³ represent hydrogen, and/or, if desired, a resulting end product of the formula I in which B represents Cb and AA¹, AA² and AA³ represent hydrogen is acylated to form a compound of the formula I in which B represents Cb and each of AA¹, $AA^2$ and $AA^3$, independently of the others, has the meaning of Ac and/or Cb, and/or, if desired, a resulting end product in which at least one of the symbols $AA^1$, $AA^2$ and $AA^3$ has one of the meanings of Cb and B represents an amino-protecting group X is converted, by removing this amino-protecting group, into a corresponding compound of the formula I in which B is hydrogen, or into a salt thereof, and/or, if desired, a free compound of the formula I having salt-forming properties is converted into a salt and/or a compound of the formula I is freed from such a salt.

The acylation according to the invention of the above-defined starting materials of the formula II, especially of desferrioxamine B or of a derivative thereof protected at the amino group, is carried out in a manner known per se using conventional general methods, it being possible, by a suitable choice of acylating agents and reaction conditions, to control to a large degree the extent of substitution with regard to the number and type of acyl radicals introduced.

If, for example, a symmetrical anhydride (that is to say, a dicarbonate) of the formula Cb.O.Cb, or preferably an asymmetrical anhydride with an inorganic acid, especially a carbonic acid monohalide, such as, more especially, a chloroformic acid ester of the formula CbCl, is used as the reactive carbonic acid derivative for the acylation according to the invention, and if the operation is carried out in the presence of a strongly basic acid-binding agent, products of the formula I that carry the oxycarbonyl groups Cb (or $Cb^1$, $Cb^2$ and $Cb^3$) both at the nitrogen and at the oxygen atoms are normally obtained. The mentioned acylating agents are normally used in undiluted form or dissolved in a minimum amount of an inert solvent, such as a chlorinated hydrocarbon (for example chloroform or dichloromethane), and the reaction temperature is normally from approximately 0° to approximately 50° C., especially approximately room temperature or slightly above that temperature. The reaction is carried out under basic conditions in a pH range of from approximately 8 to approximately 12, especially from approximately 8.5 to approximately 9.5, using strong bases; there may be used as strong bases inorganic bases, such as alkali metal carbonates and especially alkali metal hydroxides (for example soda and potash or sodium or potassium hydroxide), especially in an aqueous solution, such as an approximately 2N- to approximately 8N-, preferably 4N- to 6N-solution, which is added in portions to the reaction mixture in the same step as the acylating agent while maintaining the required pH range indicated above. A greater excess of alkaline agent, and a greater pH than approximately 10, is to be avoided, especially over relatively long periods. In order to maintain the necessary basicity, it is also possible to use strong organic bases, such as, especially, 1,8-diazabicyclo[5.4.0]undec-7-ene and similar cyclic bases; these have the advantage on the one hand that the reaction can generally proceed in a homogeneous reaction medium and, on the other hand, that a temporary excess of base is not detrimental since such bases impair neither the acylating agent nor the reaction products. Very suitable organic bases for the acylation with excess chloroformic acid esters are also tertiary amines, for example triethylamine, ethyldiisopropylamine, tributylamine, N,N-dimethyl- and N,N-diethyl-aniline, N methyl- and N-ethyl piperidine or -morpholine and N,N'-dimethylpiperazine. While maintaining the above conditions, in addition to the terminal amino group all the free hydroxy groups of the starting material are also acylated. Uniform N,O,O',O"-tetraacylates or O,O',O"-triacylates are preferably produced, that is to say, compounds of the formula I in which $AA^1$, $AA^2$ and $AA^3$, and optionally also B, all represent the same oxycarbonyl radical Cb. In that case, the acylation is carried out under the above general conditions using the equimolar amount of 4 or 3 equivalents respectively (or a smaller excess) of a uniform acylating agent.

If, however, a mixed tetra- or tri-acylate is desired in which, especially, $AA^1$, $AA^2$ and $AA^3$ do not all represent the same acyl radical but have different meanings of $Cb^1$, $Cb^2$ and $Cb^3$, the procedure is, for example, that a reaction is carried out with a mixture of several acylating agents of the same type (for example chlorides) in which 2 or 3 different acyl radicals are present in equimolar ratio, for example with a mixture of chloroformic acid esters with linear aliphatic radicals of different lengths, such as those emphasised above. Alternatively, it is also possible to react separately, in succession, with equivalent amounts of individual acylating agents (for example those mentioned above), the reaction generally being continued without isolating partially acylated intermediates. In the case of both process variants, the product obtained is a mixture of isomeric triacylates in which the individual oxycarbonyl radicals cannot be assigned to any specific one of the three oxygen atoms; as a rule, a mixture of this type is used as such without separating individual components. As already discussed above, individual oxycarbonyl radicals make their individual structural contribution to the general chemical and biological properties of an acylate almost irrespective of the specific oxygen atom at which they are localised and, accordingly, the properties of a mixed triacylate, and also of an isomeric mixture of such mixed triacylates, will correspond largely to the statistical average of the individual contributions of the acyl radicals involved. Mixed N,O,O',O"-tetraacylates and especially O,O',O"-triacylates of the formula I, and their isomeric mixtures, therefore have the same possible uses, whether as intermediates or as therapeutic active ingredients, as the analogous triacylates with uniform oxycarbonyl radicals. Accordingly, these mixed tetra- and tri-acylates, provided they contain at least one oxycarbonyl radical, may contain, instead of the radicals $Cb^1$, $Cb^2$ and/or $Cb^3$, alternatively carboxylic acid acyl radicals $Ac^1$, $Ac^2$ and $Ac^3$ with the above-mentioned meanings.

By suitable choice of the reaction conditions, the acylation according to the invention can also be so conducted that, predominantly, or even practically exclusively, a selective acylation of the terminal amino group is achieved. In the case of this variant, there is used as starting material especially desferrioxamine B or one of its acid addition salts, and an end product of the formula I is obtained in which B represents Cb and $AA^1$, $AA^2$ and $AA^3$ each represents hydrogen. (Such compounds, especially those in which B is an oxycarbonyl radical $Cb_o$ that can be used as amino-protecting group, are advantageous intermediates for further conversion, especially acylation, of the free hydroxy groups, optionally with subsequent removal of the protecting group $Cb_o$). If the operation is carried out carefully, especially if relatively low temperatures (preferably in the range of from 0° C. to room temperature) and a short reaction time are maintained, a satisfactory selective N-acylation is achieved even with the abovementioned energetically reactive carbonic acid derivatives, such as halides (especially chloroformic acid esters) or symmetrical anhydrides (dicarbonates, for example the di-tert.-butyl dicarbonate of the formula 'tC$_4$H$_9$.O.CO.O.CO.O.t-C$_4$H$_9$), especially using a bare equivalent amount of the acylating agent or a slight excess thereof. If desired, even greater selectivity can be achieved if an active ester of the formula R$_o$—O—CO—Z in which R$_o$ has the above-mentioned meaning and Z is an activating group, such as an optionally substituted (for example, methyl-, methoxy-, halogen- and, especially, nitro-, such as especially 4-nitro-substituted) phenoxy radical, is used as the reactive carbonic acid derivative. Regardless of the acylating agent used, the acylation is carried out with a slight basicity, that is to say in the presence of an acid-binding agent whose basicity is sufficient to maintain the terminal amino group to be acylated in a non-protonated state. Suitable agents of this type are non-acylatable organic bases, such as tertiary amines (for example those mentioned above) and especially nitrogen-containing heteroaromatic bases (for example quinoline, collidine and, especially, pyridine).

All the variants of the acylation process according to the invention discussed above are carried out in inert organic solvents or in aqueous medium; for better mixing of the different components, which are often sparingly soluble or miscible with one another, the operation is preferably carried out with intensive stirring and with the addition of inert water-miscible organic solvents or advantageous mixtures thereof, such as cyclic ethers (for example dioxan or tetrahydrofuran), tertiary amides (for example N,N-dimethylformamide, N,N-dimethylacetamide, N-methylpyrrolidone and hexamethylphosphorus triamide), dimethyl sulphoxide, acetonitrile, and also tertiary amines (for example those mentioned above) or acetonitrile or similar lower alkyl cyanides.

The subsequent O-acylation according to the invention, that is to say the conversion of the end products of the formula I in which at least one of the symbols represents hydrogen into products in which these symbols represent Ac$^1$ or Cb$^1$, Ac$^2$ or Cb$^2$, or Ac$^3$ or Cb$^3$, is carried out operating in an analogous manner and under the same reaction conditions as the energetic acylating variant described above (including the mixed acylations); accordingly, however, there are used as acylating agents not only the asymmetrical and symmetrical anhydrides of carbonic acid monoesters derived from the radical Cb and characterised above, but also corresponding reactive derivatives of carboxylic acids derived from the radical Ac, such as especially symmetrical anhydrides of the formulae Ac$^1$-O-Ac$^1$, Ac$^2$-O-Ac$^2$ and Ac$^3$-O-Ac$^3$, or preferably asymmetrical anhydrides with inorganic acids, especially acyl halides, especially acyl chlorides, of the formulae Ac$^1$Y, Ac$^2$Y and Ac$^3$Y in which Ac$^1$, Ac$^2$ and Ac$^3$ have the meanings indicated at the beginning and Y represents bromine or preferably chlorine. In the special case of formic acid, its mixed anhydride with acetic acid or especially with trifluoroacetic acid is preferred. In order to manufacture the above-mentioned valuable O,O',O''-triacylates, there are subjected to this conversion especially products of selective N-acylation, more especially end products of the formula I in which AA$^1$, AA$^2$ and AA$^3$ all represent hydrogen and B represents Cb, especially Cb$_o$.

The subsequent removal according to the invention of the 0-acyl radicals by ammonolysis, by means of which there are obtained, starting from resulting end products of the formula I in which B represents Cb and at least one of the symbols AA$^1$, AA$^2$ and AA$^3$ represents Ac or Cb, end products in which AA$^1$, AA$^2$ and AA$^3$ all represent hydrogen, is also carried out in a conventional manner known per se. Normally a suspension, or preferably a solution, in an inert organic solvent, of the O-acylate to be reacted is treated, especially in the absence of water, with dry ammonia gas (preferably with an excess thereof) at temperatures of from approximately 0° to approximately 45° C., especially in the region of room temperature, and at atmospheric pressure. Suitable solvents are, for example, halogenated lower alkanes (such as dichloromethane, chloroform and 1,2-dichloroethane), lower alkanols (such as, especially, methanol, ethanol, isopropyl alcohol and tert.-butyl alcohol), aliphatic and heterocyclic ethers (such as diethyl ether and 1,2-dimethoxyethane or tetrahydrofuran and dioxan, respectively), aliphatic amides of the acetamide and N,N-dimethylformamide type, and acetonitrile and similar lower alkyl cyanides, and advantageous mixtures thereof. This subsequent conversion proves especially advantageous in cases where the above-described acylation methods do not give uniform results since, for example, in the case of an undesired N-acylation, they also attack some of the free hydroxy groups in the starting material, or, in the case of total acylation, they yield only incompletely acylated products.

The subsequent removal according to the invention of the protecting group X is also carried out in the generally known manner, specific conditions for individual types of structure being described in great detail in the relevant literature (see, for example, Houben-Weyl, loc. cit.). The acidolysis (including acidic hydrolysis) is carried out, for example, with trifluoroacetic acid, hydrogen fluoride, hydrogen bromide and hydrogen chloride, optionally in the presence of water, such as with hydrochloric acid, and, in the case of acid-sensitive protecting groups, also with a lower aliphatic carboxylic acid, such as formic acid and/or acetic acid, optionally in the presence of water and/or a polyhalogenated lower alkanol or lower alkanone, such as 1,1,1,3,3,3-hexafluoropropan-2-ol or hexafluoroacetone. The groups that can be removed under neutral conditions, especially those that contain benzyl radicals, are preferably removed by hydrogenolysis, for example by hydrogenation with palladium catalysis. The $\beta$-silylethoxycarbonyl groups are preferably removed using agents that yield fluoride ions, for example using fluorides of quaternary organic bases, such as tetraethylammonium fluoride or tetrabutylammonium fluoride, in neutral organic solvents.

Depending on the method of operation, the end products of the formula I having an unsubstituted terminal amino group are obtained in the form of bases or acid addition salts. The bases can be obtained from the acid addition salts in a manner known per se. In turn, acid addition salts that can be used therapeutically can be obtained from the bases by reaction with acids, for example with those that form the abovementioned salts.

The most important starting materials of the formula II, such as especially desferrioxamine B and its acid addition salts, are known and those that are not known, such as a few derivatives of desferrioxamine B having a protected amino group, especially those in which in the formula II the symbol X$_o$ has a meaning other than radicals Cb$_o$, can be obtained in a manner known per se using general methods, such as those that are customary, for example, especially in peptide chemistry. The process is carried out, for example, especially in such a manner that the free amino group in the unsubstituted desferrioxamine B is blocked by the desired protecting group, for example by treating desferrioxamine B (in the form of the free base or of an acid addition salt) with a reagent that introduces the amino-protecting group, preferably under conditions that result in the selective functionalisation of the amino group while maintaining free hydroxy groups. This is effected especially, for example, by reaction with a reagent of the formula $X_oY$ in which Y represents halogen, especially chlorine, and $X_o$ represents the protecting group that is to be introduced, such as especially trityl or (optionally substituted) phenylsulphenyl, under known general conditions.

The chloroformic acid esters that are preferably to be used for the esterification, where not already known, can be obtained in a conventional manner that is known per se, for example by treating a corresponding . alcohol or glycolic monoether with an equivalent amount of phosgene, optionally in the presence of a nonacylatable amine (such as one of those mentioned hereinbefore). The methods for the manufacture of other reactive acylating agents, for example active esters, are also generally known.

In the process of the present invention there are preferably used those starting materials which result in the compounds described at the beginning as being especially valuable.

The invention also relates to those embodiments of the process in which a compound obtainable as intermediate at any stage of the process is used as starting material and the remaining process steps are carried out or a starting material is formed under the reaction conditions or is used in the form of a derivative thereof, for example in the form of a salt.

The present invention also relates to pharmaceutical compositions that contain as active ingredient one of the novel pharmacologically active compounds of the formula I, especially one of those mentioned hereinbefore for that use. Especially preferred are preparations and compositions for enteral, such as especially oral administration. The preparations contain the active ingredient alone or preferably together with a pharmaceutically acceptable carrier. The dosage of the active ingredient depends on the disease to be treated, on the species, age, weight and individual condition, and upon the method of administration.

The pharmaceutical compositions contain from approximately 5% to approximately 95% active ingredient, forms of administration given in single doses containing preferably from approximately 20% to approximately 90% and forms of administration given in non-single doses containing preferably from approximately 5% to approximately 20% active ingredient; pharmaceutical preparations in dosage unit form, such as dragées, tablets or capsules, contain from approximately 0.05 g to approximately 2.0 g, preferably from approximately 0.1 g to approximately 1.0 g, of active ingredient.

The pharmaceutical compositions of the present invention are manufactured in a manner known per se, for example by means of conventional mixing, granulating, confectioning, dissolving or lyophilising processes. For example, it is possible to obtain pharmaceutical compositions for oral administration by combining the active ingredient with one or more solid carriers, optionally granulating a resulting mixture, and processing the mixture or granulate, if desired and/or appropriate with the addition of additional adjuncts, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starches, for example, corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional adjuncts are especially flow-regulating agents and lubricants, for example silica, talc, stearic acid or salts thereof, such as magnesium stearate or calcium stearate, and/or polyethylene glycol.

Dragée cores are provided with suitable coatings that may be resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures or, for the production of coatings that are resistant to gastric juices, solutions of suitable cellulose preparations, such as acetylcellulose phthalate or hydoxypropylmethylcellulose phthalate. Colourings or pigments can be added to the tablets or dragée coatings, for example for identification purposes or to indicate different doses of active ingredient.

Further orally administrable pharmaceutical preparations are dry-filled capsules consisting of gelatine and also soft, sealed capsules consisting of gelatine and a plasticiser, such as glycerine or sorbitol. The dry-filled capsules may contain the active ingredient in the form of a granulate, for example in admixture with fillers, such as corn starch, binders and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

Further forms for oral administration are, for example, syrups prepared in customary manner which contain the active ingredient, for example, in suspended form and in a concentration of from approximately 5% to 20%, preferably approximately 10%, or in a similar concentration that produces, for example when dispensing 5 or 10 ml, a suitable single dose. There also come into consideration, for example, pulverulent or liquid concentrates for the preparation of shakes, for example in milk. Such concentrates can also be packed in single-dose quantities.

The invention also relates to a method for the treatment of diseases in which, as described hereinbefore, there is an excess of iron(III) or aluminium in the body, characterised in that a prophylactically or therapeutically effective amount of a compound of the formula I is administered, preferably perorally. There are used especially the above-mentioned pharmaceutical compositions, a daily dose of from approximately 0.5 g to approximately 15 g, preferably from approximately 1.5 g to approximately 7.5 g, of a compound of the present invention being administered to a warm-blooded animal weighing approximately 70 kg.

The following Examples illustrate the present invention; temperatures are given in degrees Celsius.

EXAMPLE 1

N-tert.-butoxycarbonyl-desferrioxamine B 10.6 g (100 mmol) of anhydrous sodium carbonate and 26.6 ml (123 mmol) of di-tert.-butyl dicarbonate are added to a suspension of 59.7 g (100 mmol) of desferrioxamine B-hydrochloride in 900 ml of a mixture (v/v) of dioxan/water (2:1) and the whole is stirred for 1.75 hours at 35°–40°. The resulting clear pale-yellow solution is concentrated to dryness in vacuo at approximately 50° (bath temperature); the crystalline residue is suspended at 50° in 150 ml of methanol and cooled, 1 liter of diethyl ether is added, and the whole is left to stand for 0.5 hours at 22°. The crystals are filtered off with suction and washed with 500 ml of diethyl ether, yielding 59.9 g of the title compound, m.p. 133°–137°; from the concentrated mother liquor it is possible to obtain in an analogous manner with methanol/diethyl ether a further 8.7 g of crystals of a less pure product.

It is also possible to process desferrioxamine B-methanesulphonate in an analogous manner and with the same result.

EXAMPLE 2

N-tert.-butoxycarbonyl-O.O′,O″-tripivaloyl-desferrioxamine B 9.2 ml (75 mmol) of pivalic acid chloride are added at 0° to a solution of 9.9 g (15 mmol) of N-tert.-butoxy-desferrioxamine B (see Example 1) in 25 ml of absolute N,N-dimethylformamide and 8.9 ml (60 mmol) of 1,8-diazabicyclo[5.4.0]undec-7-ene and the whole is stirred, without further cooling, for 4 hours at room temperature. The reaction solution is poured, while stirring, into a mixture of 300 ml each of 0.3 molar aqueous dipotassium hydrogen phosphate solution and ethyl acetate. After saturation with sodium chloride, the phases are separated and the lower phase is extracted a further twice with ethyl acetate. The organic extracts are washed with 0.3 molar dipotassium hydrogen phosphate solution and with saturated sodium chloride solution, dried over sodium sulphate and concentrated by evaporation in vacuo to yield the resinous crude product. Chromatography on 30 times the amount of silica gel yields the desired title compound in the fractions eluted with methylene chlorine/methanol (95:5).

Thin layer chromatography (silica gel): $R_f$: 0.40–0.45; toluene/acetone (4:6).

EXAMPLE 3

N-tert.-butoxycarbonyl-O,O′,O″-triacetyldesferrioxamine B

In a manner analogous to that described in Example 2 and using the same amounts of the components, N-tert.-butoxycarbonyl-desferrioxamine B (see Example 1) is reacted with 7.5 mmol of acetyl chloride and processed to form N-tert.-butoxycarbonyl-O,O′,O″-triacetyl-desferrioxamine B.

Thin layer chromatography (silica gel): $R_f$: 0.40–0.45; toluene/acetone (4:6).

EXAMPLE 4

N-tert.-butoxycarbonyl-O,O′,O″-tribenzoyldesferrioxamine B

In a manner analogous to that described in Example 2 and using the same amounts of the components, N-tert.-butoxycarbonyl-desferrioxamine B (see Example 1) is reacted with 7.5 mmol of benzoyl chloride and converted into N-tert.-butoxycarbonyl-O,O′,O″-tribenzoyldesferrioxamine B.

Thin layer chromatography (silica gel): $R_f$: 0.40–0.45; toluene/acetone (4:6).

EXAMPLE 5

N-tert.-butoxycarbonyl-O,O′,O″-trioctanoyldesferrioxamine B

An intensively stirred suspension of 13.22 g (20 mmol) of N-tert.-butoxycarbonyl-desferrioxamine B (see Example 1) in 100 ml of dichloromethane, 500 ml of tetrahydrofuran, 250 ml of dioxan and 11.2 ml (80 mmol) of triethylamine is treated dropwise at 23° C., for 25 minutes, with a solution of 12.1 ml (70.7 mmol) of octanoyl chloride in 20 ml of dichloromethane and, in addition, is stirred at room temperature for a further 6 hours. The solvents are removed in a water-jet vacuum, and the residue is mixed with 50 ml of water and extracted with ethyl acetate. The organic extracts are dried with sodium sulphate, freed of solvent in vacuo, dissolved in dichloromethane and chromatographed on silica gel. By eluting with mixtures of dichloromethane/isopropyl alcohol (95:5) and distilling off the solvents, the desired N-tert.-butoxycarbonyl-O,O′,O″-trioctanoyl-desferrioxamine B is obtained in the form of a thick oil, which gradually solidifies to crystals, m.p. 47°–50° C.

Thin layer chromatography (silica gel): $R_f$: 0.27; chloroform/acetone (70:30).

EXAMPLE 6

N-O,O′,O″-tetraethoxycarbonyl-desferrioxamine B 209 ml (1.5 mol) of triethylamine are added to a suspension of 98.4 g (0.15 mol) of desferrioxamine B-methanesulphonate in 1500 ml of acetonitrile and 3000 ml of methylene chloride and, while stirring at 10° C., the whole is treated dropwise over a period of 30 minutes with a solution of 144 ml (1.5 mol) of chloroformic acid ethyl ester in 200 ml of methylene chloride. The reaction mixture is stirred for a further 3 hours at room temperature and freed of readily volatile components in a water-jet vacuum. The residue is stirred with 1 liter of phosphate buffer of pH 8.0, adjusted to pH 7.4 and taken up in methylene chloride. By distilling off the organic solvent, the desired title compound is obtained as a homogeneous product in the form of a yellow oil.

Thin layer chromatography (silica gel): $R_f$: 0.26; methylene chloride/isopropyl alcohol (9:1) 0.82; chloroform/methanol (4:1).

EXAMPLE 7

N-ethoxycarbonyl-desferrioxamine B

Dry ammonia gas is introduced at room temperature, for 5 hours, into a solution of 127.0 g (0.15 mol) of crude N,O,O′,O″-tetraethoxycarbonyl-desferrioxamine B (see Example 6) in 2 liters of methylene chloride. The reaction mixture is concentrated and the crystalline residue is crystallised from ethyl acetate. The resulting title compound, m.p. 157°–158° C., is homogeneous according to thin layer chromatogrpahy:
[silica gel; $R_f$: 0.20 in methylene chloride/isopropyl alcohol (9:1) and 0.65 in chloroform/methanol (4:1)].

EXAMPLE 8

N-ethoxycarbonyl-O,O',O''-trioctanoyldesferrioxamine B 11 ml (80 mmol) of triethylamine are added to a suspension of 12.6 g (20 mmol) of N-ethoxycarbonyldesferrioxamine B in 500 ml of acetonitrile and 300 ml of methylene chloride and, while stirring at 22° C., the whole is treated dropwise over a period of 30 minutes with a solution of 12 ml (72 mmol) of octanoyl chloride in 20 ml of methylene chloride. The reaction mixture is stirred at temperatures of between 30° C. and room temperature for a further 5 hours and freed of readily volatile components by distillation in a water-jet vacuum; the residue is stirred with water, adjusted to pH 3.0 with glacial acetic acid and taken up in ethyl acetate. Concentration of the organic phase yields the crude product in the form of a yellow-reddish oil. This is dissolved in methylene chloride and chromatographed on a silica gel column; the fractions eluted with a mixture of methylene chloride/isopropyl alcohol (95:5), after the solvents have been distilled off, yield the desired title compoud in the form of an almost colourless oil, which is homogeneous according to thin layer chromatography.

Thin layer chromatography (silica gel): $R_f$=0.21; methylene chloride/isopropyl alcohol (9:1); 0.80 chloroform/methanol (4:1).

EXAMPLE 9

N-tert.-butoxycarbonyl-O,O',O''-tri-(2-methoxyethoxycarbonyl)-desferrioxamine B
[N-tert.-butoxycarbonyl-O,O',O''-tri-(3-oxabutoxycarbonyl)-desferrioxamine B]

A solution of 693 mg (5.0 mmol) of 2-methoxyethyl chloroformate in 1.0 ml of methylene chloride is added at 23° C. over a period of 2 minutes to a suspension of 662 mg (1.0 mmol) of N-tert.-butoxy-desferrioxamine B (see Example 1) in 25 ml of tetrahydrofuran, 6 ml of methylene chloride and 0.56 ml (4.0 mmol) of triethylamine and the mixture is stirred for 45 minutes at room temperature. Volatile components of the reaction mixture are distilled off in vacuo, and the solid residue is taken up in 20 ml of water and extracted with ethyl acetate. By distilling off the solvent from the organic extracts a crude product is obtained which is applied in methylene chloride solution to a silica gel column. Elution with a mixture of methylene chloride/isopropyl alcohol (92:8) yields fractions which, after the solvents have been distilled off, yield the desired title compound in the form of a colourless oil which is homogeneous according to thin layer chromatography.

Thin layer chromatography (silica gel): $R_f$: 0.05 in chloroform/acetone (70:30), 0.4 in methylene chloride/isopropyl alcohol (90:10) and 0.85 in methylene chloride/methanol (80:20).

The 2 methoxyethyl choroformate used as reagent can be obtained in the following manner:

A mixture of 39.6 ml (0.5 mol) of 2-methoxyethanol and 73.5 ml (0.53 mol) of triethylamine is added dropwise to 520 ml of a 20% solution of phosgene in toluene (corresponding to 98.9 g, that is 1.0 mol, of phosgene) over a period of 45 minutes, while cooling to from 5° to 10° C. and while stirring, and the mixture is stirred for a further hour at room temperautre. The excess phosgene is removed by passing a stream of nitrogen through at from 30° to 40° C. and collected with an aqueous 4N sodium hydroxide solution. The reaction mixture is fractionated in vacuo; the desired 2-methoxyethyl chloroformate is obtained in the form of a colourless liquid boiling at 59°–61° C./16 torr (/2133 Pas) in a yield of 20.9 g (30 % of the theoretical yield).

EXAMPLE 10

N-tert.-butoxy-O,O',O''-tri-[2-(2-methoxyethoxy)-ethoxycarbonyl]-desferrioxamine B
[N-tert.-butoxy-O,O',O''-tri-(3,6-dioxaheptyloxycarbonyl)-desferrioxamine B]

In a manner analogous to that described in Example 9, there is added to the same amounts of the desferrioxamine B compound and auxiliary substances a solution of 922 mg (5.05 mmol) of 2-(2-methoxyethoxy)-ethyl chloroformate in 3.5 ml of toluene, and the whole is stirred at room temperature for 4 hours and worked up. The crude product is purified chromatographically in the same manner as in Example 9 and yields the title compound in the form of a colourless oil that is homogeneous according to thin layer chromatography.

Thin layer chromatography (silica gel): $R_f$: 0.03 in chloroform/acetone (70:30) 0.23 in methylene chloride/isopropyl alcohol (90:10) and 0.77 in methylene chloride/methanol (80:20).

The 2-(2-methoxyethoxy)-ethyl chloroformate used as reagent can be manufactured by the general process described in connection with Example 9, but with 60 ml (0.5 mol) of 2-(2-methoxyethoxy)-ethanol as alcohol component.

EXAMPLE 11

O,O',O''-tri-(3-oxabutoxycarbonyl)-desferrioxamine B-hydrochloride 80 ml of an anhydrous 0.5N solution of hydrogen chloride in methylene chloride are added to a solution of 7.64 g (7.9 mmol) of N-tert.-butoxycarbonyl-O,O',-O''-tri-(3-oxabutoxycarbonyl)-desferrioxamine B (see Example 9) in 80 ml of methylene chloride and the whole is stirred for 2.5 hours at 22°. The reaction mixture is diluted with 80 ml of ethyl acetate and substantially concentrated in vacuo. The residue is digested with mixtures of ether/petroleum ether and chromatographed on silica gel; elution with a mixture of methylene chloride/methanol (80:20) yields the title compound in a practically pure state.

Thin layer chromatography (silica gel): $R_f$: 0.52–0.55 in chloroform/methanol (9:1).

EXAMPLE 12

O,O',O''-tri-(3,6-dioxaheptyloxycarbonyl)-desferrioxamine B-trifluoroacetate 6.0 ml (80.8 mmol) of trifluoroacetic acid are added dropwise over a period of 3 minutes at 2° C. to a solution of 2.2 g (2.0 mmol) of N-tert.-butoxycarbonyl-O,O',O''-tri-(3,6-dioxaheptyloxycarbonyl)desferrioxamine B (see Example 10) in 10 ml of toluene and 1.5 ml (3.8 mmol) of anisole and the reaction mixture is stirred for one hour at a temperature below 10° C. The solvent is removed and the residue is dried in a high vacuum at 45°–50° C. until a constant weight is reached, resulting in the title compound.

Thin layer chromatography (silica gel): $R_f$: 0.02; chloroform/acetone (70:30).

EXAMPLE 13

Manufacture of 1000 capsules, each capsule containing 260 mg of active ingredient (that is of the product according to one of Examples 1–12)

| Composition | |
|---|---|
| active ingredient | 260 g |
| talc | 36 g |
| wheat starch | 24 g |
| magnesium stearate | 16 g |
| lactose | 4 g |
| | 340 g |

Preparation

The pulverulent substances are forced through a sieve having a mesh width of 0.6 mm and thoroughly mixed. Gelatine capsules are prepared with 340 mg each of this mixture using a capsule-filling machine.

EXAMPLE 14

Manufacture of 1000 capsules, each capsule containing 105 mg of the active ingredient (that is of the product according to one of Examples 1–12).

| Composition | |
|---|---|
| Active ingredient | 105 g |
| ethylcellulose | 3 g |
| stearic acid | 3 g |
| | 111 g |

Preparation

The ethylcellulose and the stearic acid are dissolved in 120 ml of methylene chloride, the active ingredient is added, and the mass is forced through a sieve having a mesh width of 0.6 mm at a temperature of approximately 40°, during which the methylene chloride evaporates. 111 mg of the resulting granulate are introduced into 0.5 ml gelatine capsules using a capsule-filling machine.

I claim:

1. An acylate of desferrioxamine B of the formula

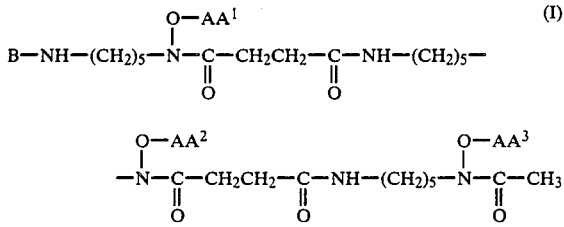

wherein at least one of the radicals $AA^1$, $AA^2$, $AA^3$ and B is tert.-butyloxycarbonyl, allyloxycarbonyl, 2-(trimethylsilyl)-ethoxycarbonyl or a radical of the formula lower alkyl($-O-CH_2-CH_2-$)$_n$$O-CO-$ wherein n represents 1 to 4, and each of the remaining radicals $AA^1$, $AA^2$, $AA^3$ and B, independently of the others, represents alkanoyl having up to 20 carbon atoms, benzoyl or hydrogen, or a salt of said acylate having salt-forming properties.

2. A compound according to claim 1 wherein at least one of the radicals $AA^1$, $AA^2$, $AA^3$ and B is tert.-butyloxycarbonyl, allyloxycarbonyl, 2-(trimethylsilyl)-ethoxycarbonyl or a radical of the formula lower alkyl-($-O-CH_2-CH_2-$)$_n$$O-CO-$ wherein n represents 1 to 4 and each of the remaining radicals $AA^1$, $AA^2$, $AA^3$ and B, independently of the others, represents alkanoyl having up to 20 carbon atoms or benzoyl.

3. A compound according to claim 1 wherein B is hydrogen and each of the radicals $AA^1$, $AA^2$ and $AA^3$ is tert.-butyloxycarbonyl, allyloxycarbonyl, 2-(trimethysilyl)-ethoxycarbonyl or a radical of the formula lower alkyl($-O-CH_2-CH_2-$)$_n$$O-CO-$ wherein n represents 1 to 4, or a pharmaceutically acceptable acid addition salt thereof.

4. A compound according to claim 1 wherein B is tert.-butyloxycarbonyl, allyloxycarbonyl, 2-(trimethylsilyl)-ethoxycarbonyl or a radical of the formula lower alkyl($-O-CH_2-CH_2-$)$_n$$O-CH-$ wherein n represents 1 to 4, and each of the radicals $AA^1$, $AA^2$ and $AA^3$ represents hydrogen.

5. A compound according to claim 1 wherein B is tert.-butyloxycarbonyl and each of $AA^1$, $AA^2$ and $AA^3$ is a radical of the formula lower alkyl($-O-CH_2-CH_2-$)$_n$$O-CO-$ wherein n represents 1 to 4.

6. A compound according to claim 1 wherein B is hydrogen and each of $AA^1$, $AA^2$ and $AA^3$ is a radical of the formula lower alkyl($-O-CH_2-CH_2-$)$_n$$O-CO-$ wherein n represents 1 to 4, or a pharmaceutically acceptable acid addition salt thereof.

7. A compound according to claim 1 wherein B is tert.-butyloxy-carbonyl and each of $AA^1$, $AA^2$ and $AA^3$ is 2-methoxyethoxycarbonyl.

8. A compound according to claim 1 wherein B is tert.-butyloxycarbonyl and each of $AA^1$, $AA^2$ and $AA^3$ is 2-(2-methoxyethoxy)-ethoxycarbonyl.

9. A compound according to claim 1 wherein B is tert.-butyloxy-carbonyl and each of $AA^1$, $AA^2$ and $AA^3$ is n-octanoyl.

10. A compound according to claim 1 wherein B is hydrogen and each of $AA^1$, $AA^2$ and $AA^3$ is 2-methoxyethoxycarbonyl, or a pharmaceutically acceptable acid addition salt thereof.

11. A compound according to claim 1 wherein B is hydrogen and each of $AA^1$, $AA^2$ and $AA^3$ is 2-(2-methoxy-ethoxy)-ethoxycarbonyl, or a pharmaceutically acceptable acid addition salt thereof.

12. A pharmaceutical composition for the prophylaxis or treatment of pathological conditions associated with an excess of iron(III) or aluminium or caused by iron(III)-dependent microorganism in a warm-blooded animal comprising as the active ingredient a prophylactically or therapeutically effective amount of a compound as claimed in claim 1 and a pharmaceutically acceptable carrier.

13. A pharmaceutical composition for oral administration to a warm-blooded animal in the form of a tablet, a dragée or capsule for the prophylaxis or treatment of a pathological condition associated with an excess of iron(III) or aluminium or caused by an iron(III)-dependent microorganism comprising as the active ingredient a prophylactically or therapeutically effective amount of a compound as claimed in claim 2.

14. A method for the prophylaxis or treatment of a warm-blooded animal, for pathological conditions associated with an excess of iron(III) or aluminium in the body, comprising orally administering to said animal a prophylactically or therapeutically effective amount of a compound according to claim 2 on its own or in the form of a pharmaceutical composition.

15. A method for the prophylaxis or treatment of a warm-blooded animal for pathological conditions caused by iron(III)-dependent microorganisms, comprising orally administering to said animal a prophylactically or therapeutically effective amount of a compound according to claim 2 on its own or in the form of a pharmaceutical composition.

16. N,O,O'O''-tetra-desferrioxamine B.

17. O,O',O''-tri-desferrioxamine B or a pharmaceutically acceptable acid addition salt thereof.

* * * * *

UNITED STATES PATENT AND TRADEMARK OFFICE
CERTIFICATE OF CORRECTION

PATENT NO. : 4,764,523
DATED : 08-16-88
INVENTOR(S) : Heinrich Peter

It is certified that error appears in the above-identified patent and that said Letters Patent is hereby corrected as shown below:

On the cover sheet, change "Peter Heinrich" to read:

--HEINRICH PETER--

On the title page, Item [19] "Heinrich" should read -- Peter --.

Signed and Sealed this

Sixteenth Day of January, 1990

*Attest:*

JEFFREY M. SAMUELS

*Attesting Officer*     *Acting Commissioner of Patents and Trademarks*